United States Patent [19]

Niwa

[11] Patent Number: 5,140,991
[45] Date of Patent: Aug. 25, 1992

[54] HEARTBEAT SYNCHRONOUS PULSE WAVE DETECTING APPARATUS

[75] Inventor: Minoru Niwa, Nagoya, Japan

[73] Assignee: Colin Electronics, Co., Ltd., Komaki, Japan

[21] Appl. No.: 567,769

[22] Filed: Aug. 15, 1990

[30] Foreign Application Priority Data

Aug. 22, 1989 [JP] Japan .................................. 1-215400

[51] Int. Cl.$^5$ .............................................. A61B 5/02
[52] U.S. Cl. ..................................... 128/687; 128/672
[58] Field of Search ............... 128/672, 677, 681, 687, 128/688, 689, 690

[56] References Cited

U.S. PATENT DOCUMENTS

| 4,564,020 | 1/1986 | Link ..................................... 128/688 |
| 4,667,680 | 5/1987 | Ellis ..................................... 128/687 |
| 4,893,631 | 1/1990 | Wenzel et al. ......................... 128/687 |

FOREIGN PATENT DOCUMENTS 58-149731 9/1983 Japan .

OTHER PUBLICATIONS

L. A. Geddes, "The Direct and Indirect Measurement of Blood Pressure", 1970, pp. 87-99, Yearbook Medical Publishers.
L. A. Geddes, "Characterization of the Oscillometric Method for Measuring Indirect Blood Pressure", 1982, vol. 10, pp. 271-280, Annals of Biomedical Engineering.
Kenneth Borow, M.D. and Jane Newburger, M.D., "Noninvasive Estimation of Central Aortic Pressure Using the Oscillometric Method for Analyzing Systemic Artery Pulsatile Blood Flow", 1982, pp. 879-886, The C. V. Mosby Co.

Primary Examiner—Francis Jaworski
Assistant Examiner—Scott R. Akers
Attorney, Agent, or Firm—Oliff & Berridge

[57] ABSTRACT

An apparatus for detecting a pulse wave produced from a subject in synchronous relationship with heartbeats of the subject, including a probe device for sensing a heartbeat synchronous pulse wave transmitted thereto and generating a signal representative of the sensed pulse wave, a sampling device for periodically determining a magnitude of the signal, a determining device for determining a lower peak and a following upper peak of the heartbeat synchronous pulse wave based on variation of the magnitudes determined by the sampling means, a calculating device for calculating a value by subtracting, from each of the magnitudes determined by the sampling means, a magnitude of the signal determined by the sampling means prior by a predetermined number of periods to the each of the magnitudes, and a judging means for judging whether or not the following upper peak is a proper upper peak of a pulse of the heartbeat synchronous pulse wave, based on the values calculated by the calculating means with respect to a portion of the signal between the lower peak and the following upper peak.

13 Claims, 8 Drawing Sheets

HEARTBEAT SYNCHRONOUS PULSE WAVE DETECTING APPARATUS

BACKGROUND OF THE INVENTION

1. Field of the Invention

The present invention generally relates to a heartbeat synchronous pulse wave detecting apparatus and particularly to such an apparatus which correctly identifies proper upper and lower peaks of the pulse wave.

2. Problem Solved by the Invention

There is known a heartbeat synchronous pulse wave detecting apparatus having a probe which is adapted to be set on a body surface of a subject to sense a pulse wave transmitted thereto in synchronous relationship with heartbeats of the subject and generates a signal representative of the sensed heartbeat synchronous pulse wave. An arterial pulse wave detecting apparatus is one of such apparatus. As shown in FIG. 8, a heartbeat synchronous pulse wave, such as an arterial pulse wave, consists of successive pulses each of which corresponds to a heartbeat, and each pulse normally has proper (or primary) upper and lower peaks (A, D) and in addition a secondary upper peak (C) and a secondary lower peak or notch (B). The proper upper peak corresponds to the systole (or compression) of the heart, while the proper lower peak corresponds to the diastole (expansion). Those peaks periodically occur in the order of A, B, C, D, A, B, C . . .

The conventional apparatus is capable of determining upper and lower peaks of a heartbeat synchronous pulse wave. However, it suffers from a problem that it erroneously determines a secondary upper peak as a proper upper peak, and/or a notch as a proper lower peak. For example, in the event that the magnitude of a secondary upper peak is greater than that of a proper upper peak, the conventional apparatus confuses the secondary upper peak with the proper upper peak and erroneously determines the secondary upper peak as the proper upper peak.

SUMMARY OF THE INVENTION

It is therefore an object of the present invention to provide a heartbeat synchronous pulse wave detecting apparatus which correctly identifies a proper upper peak of a heartbeat synchronous pulse wave.

The above object has been achieved by the present invention, which provides an apparatus for detecting a pulse wave produced from a subject in synchronous relationship with heartbeats of the subject, the heartbeat synchronous pulse wave consisting of a plurality of successive pulses each of which corresponds to a heartbeat and has at least one upper peak including a proper upper peak and at least one lower peak including a proper lower peak, the apparatus comprising (a) probe means for sensing a heartbeat synchronous pulse wave transmitted thereto and generating a signal representative of the sensed pulse wave, (b) sampling means for periodically determining a magnitude of the signal, (c) determining means for determining a lower peak and a following upper peak of the heartbeat synchronous pulse wave, based on variation of the magnitudes determined by the sampling means, (d) calculating means for calculating a value by subtracting, from each of the magnitudes determined by the sampling means, a magnitude of the signal determined by the sampling means prior by a predetermined number of periods to the each of the magnitudes, and (e) judging means for judging whether or not the following upper peak is a proper upper peak of a pulse of the heartbeat synchronous pulse wave, based on the values calculated by the calculating means with respect to a portion of the signal between the lower peak and the following upper peak.

The heartbeat synchronous pulse wave detecting apparatus constructed as described above, the sampling means periodically determines a magnitude of the signal supplied from the probe means representative of the sensed heartbeat synchronous pulse wave, and the calculating means calculates a value by subtracting from each of the magnitudes sampled by the sampling means a magnitude of the signal sampled by the sampling means prior by a predetermined number of periods or cycles to the each of the magnitudes. In the meantime, the determining means determines a lower peak and the following upper peak of the heartbeat synchronous pulse wave based on variation in the magnitudes sampled by the sampling means, and the judging means judges whether or not the upper peak determined by the determining means is a proper upper peak of a pulse of the heartbeat synchronous pulse wave, based on the values calculated by the calculating means with respect to a portion of the signal between the lower peak and the upper peak. The judging means can also judge whether or not the lower peak is a proper lower peak, because a proper lower peak precedes a proper upper peak. Thus, the present apparatus prevents a secondary upper peak from erroneously being identified as a proper upper peak, and a notch from erroneously being identified as a proper lower peak, even in the event that the magnitude of the secondary upper peak is greater than that of the proper upper peak when the subject is undergoing Valsalva's test.

According to a feature of the present invention, the judging means comprises means for determining a value, maxSLOPE, which is the greatest value of the values, SLOPE, obtained by the calculating means with respect to the portion of the signal between the lower peak and the following upper peak.

In a preferred embodiment of the present invention, the judging means further comprises means for determining a time period, t, between commencement of the periodic magnitude sampling of the sampling means and the time of sampling of the following upper peak; means for determining a time period, ts, between commencement of the lower peak determination of the determining means and the time of sampling of the following upper peak, the lower peak determination being commenced if negative SLOPEs are obtained by the calculating means over a predetermined number of successive cycles of the periodic magnitude sampling; and means for judging whether or not the value t is greater than a value, twind, the value twind being defined by the following expression: $twind = 4/5 \times ts_{-1}$, where $ts_{-1}$ is a value ts which is determined with respect to a proper upper peak preceding the following upper peak. The judging means may further comprise means for, if the value t is judged not to be greater than the value twind, judging whether or not value maxSLOPE is greater than a value, mth, the value mth being defined by the following expression: $mth = 7/10 \times maxSLOPE_{-1}$, where $maxSLOPE_{-1}$ is a value maxSLOPE which is determined with respect to the proper upper peak preceding the following upper peak, the judging means judging that the following upper peak is not the proper upper peak, if the value maxSLOPE is judged not to be greater than the value mth. The judging means may further comprise means for, if the value t is judged to be greater than the value twind, judging whether or not the value maxSLOPE is greater than a value, mth/2, the judging means judging that the following upper peak is not the proper upper peak, if the value maxSLOPE is judged not to be greater than the value mth/2.

In another embodiment of the present invention, the judging means further comprises means for determining a value, minSLOPE, which is an absolute value of the smallest value of the values SLOPE obtained by the calculating means with respect to a portion of the signal between commencement of the lower peak determination of the determining means, and the lower peak; and means for judging whether or not the value maxSLOPE is greater than the value minSLOPE, the judging means judging that the following upper peak is not the proper upper peak, if the value maxSLOPE is judged not to be greater than the value minSLOPE.

In yet another embodiment of the present invention, the judging means further comprises means for determining a time period, dst, between the time of sampling of the lower peak and the time of sampling of the following upper peak; and means for judging whether or not the value dst is greater than a predetermined time, for example, 30 ms and smaller than a value, mds, the value mds being defined by the following expression: $mds = \frac{1}{2} \times ts_{-1}$, where $ts_{-1}$ is a value ts which is determined with respect to a proper upper peak preceding the following upper peak, the value mds falling within a range of 500 to 200 ms, the judging means judging that the following upper peak is not the proper upper peak, if the value dst is judged either not to be greater than the predetermined value, or not to be smaller than the value mds.

In a further embodiment of the present invention, the judging means further comprises means for determining a time period, ts, between commencement of the lower peak determination of the determining means and the time of sampling of the following upper peak, the lower peak determination being commenced if negative SLOPEs are obtained by the calculating means over a predetermined number of successive cycles of the periodic magnitude sampling; means for determining a time period, dst, between the time of sampling of the lower peak and the time of sampling of the following upper peak; and means for judging whether or not the value ts is greater than a predetermined value, for example, 200 ms and the value dst is smaller than a value, ts/2, the judging means judging that the following upper peak is not the proper upper peak, either if the value value ts is judged not to be greater than the predetermined value, or if the value dst is judged not to be smaller than the value ts/2.

The above indicated definitions of parameters, twind, mth, mds may be changed depending upon the characteristics of the upper peaks to be detected, such as medically significant upper peaks.

According to another feature of the present invention, the determining means comprises means for calculating a value, DIFF, by subtracting, from the each of the magnitudes determined by the sampling means, a magnitude of the signal determined by the sampling means prior by one period to the each of the magnitudes; means for determining, as the lower peak, a magnitude of the signal determined by the sampling means by which magnitude the sign of the value DIFF is changed from negative to positive; and means for determining, as the following upper peak, a magnitude of the signal determined by the sampling means by which magnitude the positive sign of the value DIFF is changed to negative. In this case, the apparatus is free from the problem of adverse influences from low frequency noise resulting from, for example, respiration of the subject.

According to yet another feature of the present invention, the apparatus further comprises means for judging whether or not the probe means is located at an appropriate position on a body surface of the subject, the means judging that the probe means is located at the appropriate position, if a value, upc, is smaller than a value, dwc, the value upc being defined as the number of positive or zero SLOPEs out of the values SLOPE obtained between commencement of the lower peak determination of the determining means, and the following upper peak, the value dwc being defined as the number of the remaining, negative SLOPEs out of the values SLOPE; and displacing means for, if the probe means is judged not to be located at the appropriate position, displacing the probe means to the appropriate position. In the event that the probe means is located at an inappropriate position such as a position directly above a bone or a tendon, the phase of the signal from the probe means is reversed and is not suitable to utilize for determining a proper upper peak. In this event, therefore, the probe means is displaced so as to obtain a signal whose phase is not reversed.

According to another feature of the present invention, the probe means comprises a single pressure sensing element, the sampling means periodically determining a magnitude of the signal generated by the single element.

According to another feature of the present invention, the probe means comprises a plurality of pressure sensing elements which are grouped into a plurality of element groups, the sampling means periodically determining a magnitude of the signal generated by each of the pressure sensing elements belonging to each of the element groups, and calculating, with respect to each of the element groups, a value by summing up the magnitudes determined by the sampling means, the calculating means calculating the value SLOPE by subtracting, from each of the summed-up values obtained by the sampling means, a summed-up value obtained by the sampling means prior by the predetermined number of periods to the each of the summed-up values, the judging means providing an affirmative judgement if, with respect to at least one of the element groups, the following upper peak is judged as the proper upper peak based on the values SLOPE obtained by the calculating means between the lower peak and the following upper peak. Alternatively, it is possible that the judging means be adapted to provide an affirmative judgement if, with respect to two or more of the element groups, the following upper peak is judged as the proper upper peak based on the values SLOPE obtained by the calculating means between the lower peak and the following upper peak. Furthermore, it is possible that the sampling means be adapted to periodically determine a magnitude of the signal generated by each of the pressure sensing elements, the calculating means be adapted to calculate a value, SLOPE, by subtracting, from each of the magnitudes determined by the sampling means, a magnitude of the signal determined by the sampling means prior by a predetermined number of periods to the each of the magnitudes, and the judging means be adapted to provide an affirmative judgement if with respect to at least one of the pressure sensing elements the following upper peak is judged as the proper upper peak based on the values SLOPE obtained by the calculating means with respect to a portion of the signal therefrom between the lower peak and the following upper peak. In these cases, if at least one element group or at least one pressure sensing element is located at an appropriate position on the subject, the present apparatus can identify a proper upper peak.

BRIEF DESCRIPTION OF THE DRAWINGS

The above and optional objects, features and advantages of the present invention will be better understood by reading the following detailed description of the presently preferred embodiment of the invention when considered in conjunction with the accompanying drawings in which.

DETAILED DESCRIPTION OF THE PREFERRED EMBODIMENT

Figure 1:
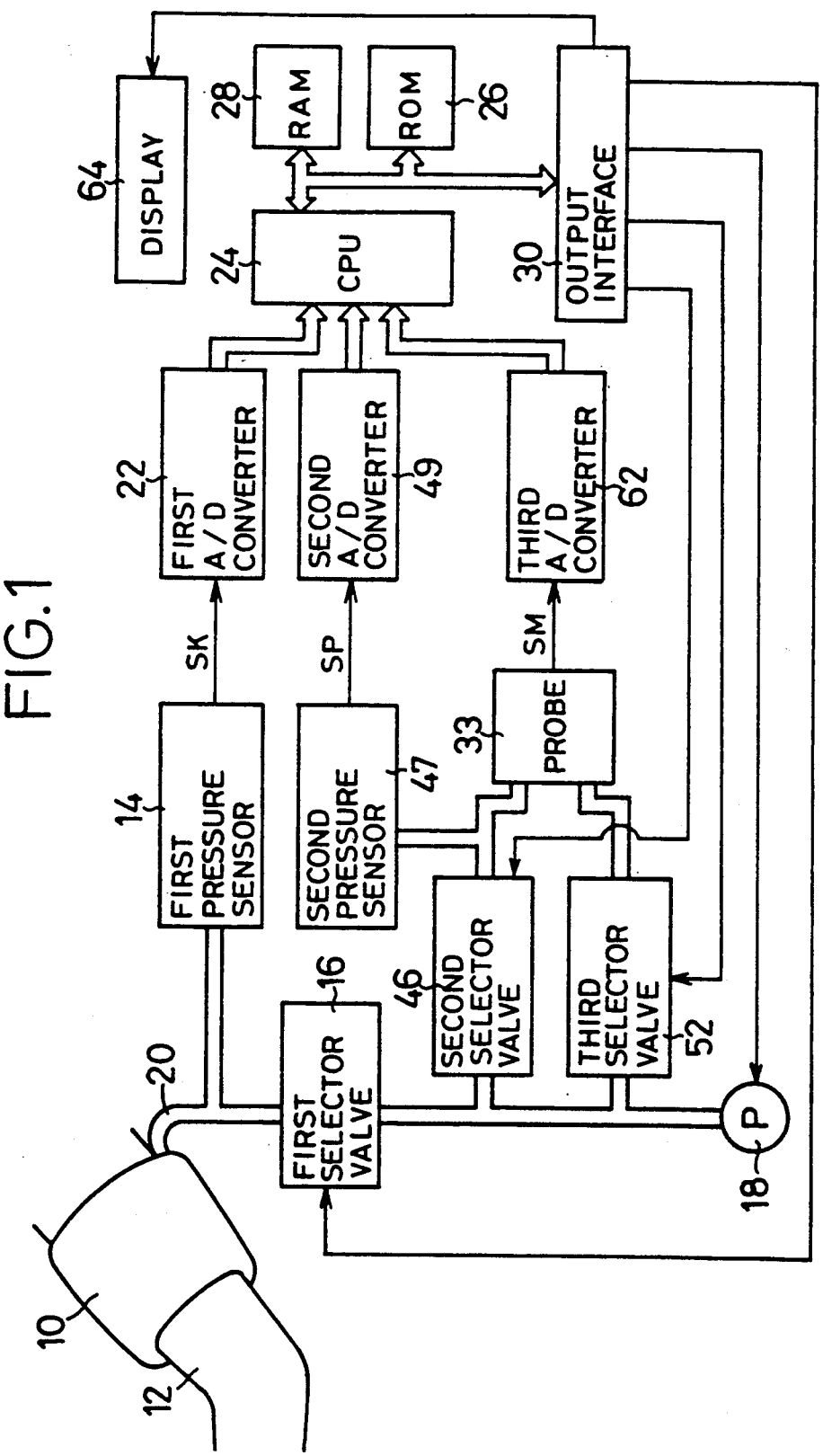
FIG. 1 is a diagrammatic view of the blood pressure monitoring system having an arterial pulse wave detecting apparatus which embodies the present invention.

Referring first to FIG. 1, there is shown a blood pressure monitoring system for monitoring blood pressure of a subject by using an arterial pulse wave detecting apparatus which embodies the present invention. Reference numeral 10 designates an inflatable cuff formed of rubber. The cuff 10 is wound around, for example, an upper arm 12 of a subject so as to occlude an underlying arterial vessel. The cuff 10 is connected via piping 20 to a first pressure sensor 14, a first selector valve 16, and an electric pump 18. The electric pump 18 supplies the cuff 10 with a pressurized fluid, for example, pressurized air so as to increase a pressure in the cuff 10 (hereinafter, referred to as the "cuff pressure"). The first pressure sensor 14 senses the cuff pressure, and generates a cuff pressure signal SK representative of the sensed cuff pressure, to a central processing unit (CPU) 24 via a first analog to digital (A/D) converter 22.

The CPU 24 is coupled via data bus to a read only memory (ROM) 26, a random access memory (RAM) 28, and an output interface 30. The CPU 24 processes signals according to program stored in the ROM 26, while utilizing the temporary-storage function of the RAM 28. In particular, the CPU 24 controls the electric pump 18 and the first selector valve 16 via drive circuits (not shown), respectively, so as to regulate the cuff pressure. In addition, the CPU 24 determines systolic and diastolic blood pressure of the subject by the so-called "oscillometric method" in which the cuff pressure is slowly decreased and the blood pressure values are determined based on variation in the amplitudes of cuff pressure fluctuations sensed in the process of slow cuff pressure decrease.

Figure 2:
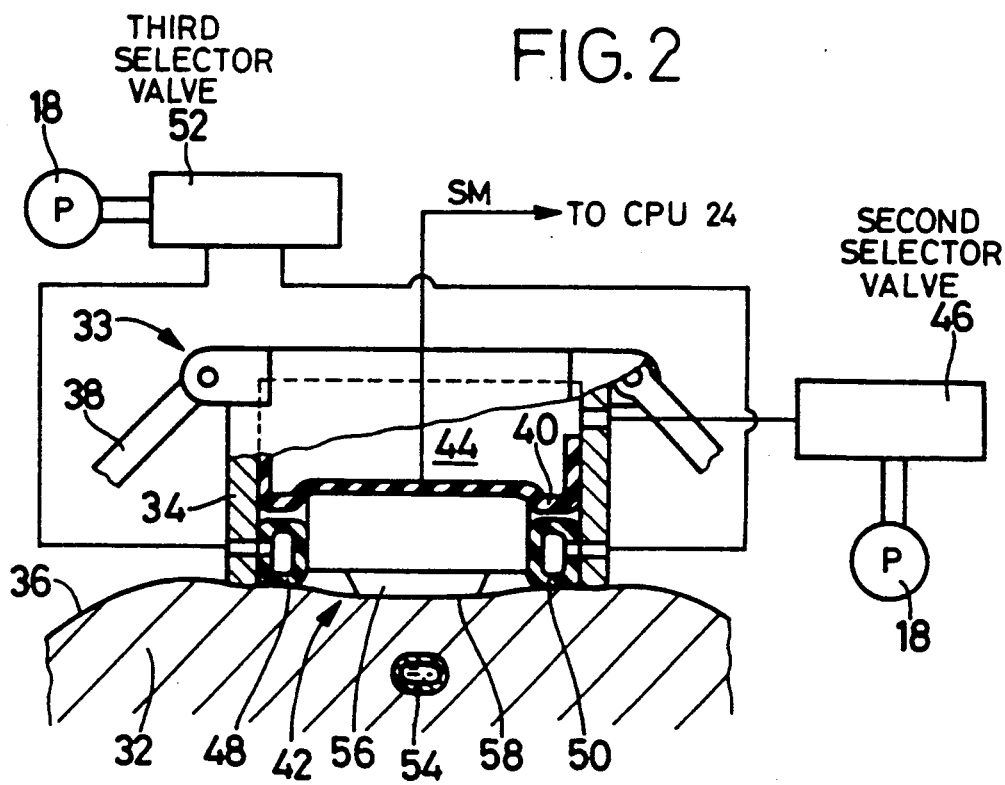
FIG. 2 is an illustrative view of a partially cut away pulse wave detector probe of the monitoring system of FIG. 1, the detector probe being set on a wrist of a subject.
Figure 3:
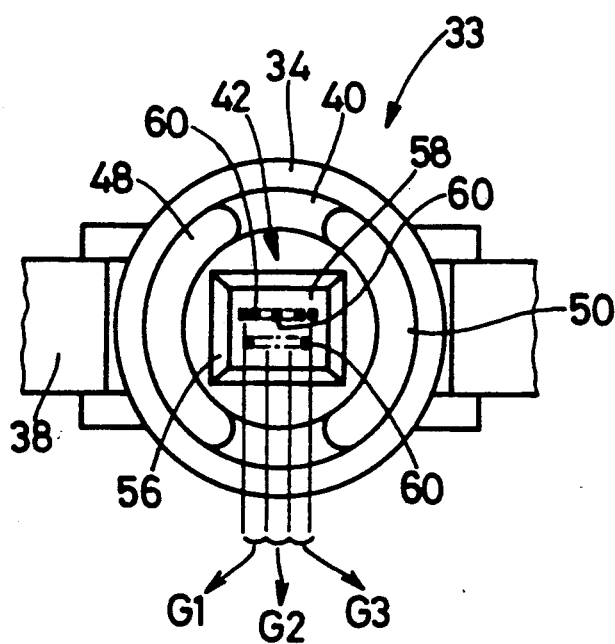
FIG. 3 is a bottom view of the detector probe of FIG. 2.

Referring next to FIGS. 2 and 3, there is shown a pulse wave detector probe 33 which is set on a wrist 32. The detector probe 33 includes a cylindrical housing 34 having an open end and a closed end or bottom wall. The detector probe 33 is detacheably worn around the wrist 32 with the help of a fastener band 38 such that the open end thereof contacts a surface 36 of the wrist 32. The detector probe 33 further includes a pulse wave sensor 42 supported by the housing 34 via a diaphragm 40 in the interior of the housing 34. The pulse wave sensor 42 is movable relative to the housing 34 in such a manner that the sensor 42 is advanceable out of the open end of the housing 34. The housing 34 and the diaphragm 40 cooperate with each other to provide a pressure chamber 44. The pressure chamber 44 is supplied with pressurized fluid from the electric pump 18 via a second selector valve 46, so that the pulse wave sensor 42 is pressed against the wrist surface 36 with a pressing force corresponding to a pressure P in the pressure chamber 44 (hereinafter, referred to as the "chamber pressure P"). The second selector valve 46 is selectively placed in a first or PRESSURE-INCREASE position in which the valve 46 permits the pressurized fluid to be supplied to the pressure chamber 44 so as to increase chamber pressure P, a second or PRESSURE-MAINTAIN position in which the valve 46 maintains chamber pressure P, and a third or PRESSURE-DECREASE position in which the valve 46 permits the fluid in the pressure chamber 44 to be discharged so as to decrease chamber pressure P. Between the second selector valve 46 and the pressure chamber 44 is provided a second pressure sensor 47 which senses chamber pressure P and generates a chamber pressure signal SP representative of the sensed chamber pressure to the CPU 24 via a second A/D converter 49.

A pair of generally arcuate rubber bags 48, 50 are provided between an inner wall of the housing 34 in the vicinity of the open end thereof, and the pulse wave sensor 42, such that the rubber bags 48, 50 are aligned with the secured ends of the fastener band 38, respectively. The rubber bags 48, 50 are fixed to both the housing 34 and the pulse wave sensor 32. The rubber bags 48, 50 are supplied with pressurized fluid from the electric pump 18 via a third selector valve 52. The third selector valve 52 is selectively placed in a first position in which the valve 52 permits the pressurized fluid to be supplied to one 48 of the rubber bags, and a second position in which the valve 52 permits the pressurized fluid to be supplied to the other rubber bag 50, so that the pulse wave sensor 32 is movable in a direction generally perpendicular to an underlying radial artery 54.

The pulse wave sensor 42 includes a semiconductor chip 56 formed of, for example, monocrystalline silicon. The chip 56 has a press surface 58 adapted to be pressed against the radial artery 54 via the wrist surface 36. A plurality of pressure sensing elements 60, for example, pressure sensing diodes are formed in the press surface 58 such that the elements 60 are arranged in two arrays 60A in an alternate manner. With the detector probe 33 set on the wrist 32, the element arrays 60A each extend generally perpendicular to the radial artery 54. Each of the elements 60 senses an arterial pulse wave, namely, oscillatory pressure wave that is produced from the radial artery 54 and transmitted to the wrist surface 36 in synchronous relationship with heartbeats of the subject, and generates a pulse wave signal SM representative of the sensed pulse wave to the CPU 24 via a third A/D converter 62. The arterial pulse wave consists of successive pulses each of which corresponds to a heartbeat. In the present embodiment, the arterial pulse wave is a heartbeat synchronous pulse wave, and pulse wave signal SM is a signal representative of a sensed heartbeat synchronous pulse wave.

The pressure sensing elements 60 are provided at regular intervals of distance as viewed in the direction of the arrays 60A thereof. The regular interval is sufficiently small so that a plurality of elements 60 can be located directly above the radial artery 54. A distance between the opposite end elements of the arrays 60A is much greater than a maximum lumen of the radial artery 54 that is assumed when the artery 54 is pressed under the pulse wave sensor 42. As shown in FIG. 3, the pressure sensing elements 60 are grouped into a first, a second and a third group G1, G2, G3 in the order of description as viewed in the direction of the arrays 60A thereof. All the element groups G1–G3 include the same number of elements 60.

According to the program stored in the ROM 26, the CPU 24 controls the second selector valve 46 via a drive circuit (not shown) so as to regulate chamber pressure P. Based on pulse wave signals SM supplied from the pressure sensing elements 60 when chamber pressure P is held at a predetermined value, the CPU 24 selects as an optimum pressure sensing element 60* one pressure sensing element 60a such that an amplitude of pulse wave signal SM* from optimum element 60*, namely, selected one element 60a is the greatest of all the amplitudes of the pulse wave signals. Further, while increasing chamber pressure P, the CPU 24 determines, based on pulse wave signal SM* from optimum element 60*, an optimum chamber pressure P* corresponding to an optimum pressing force for most suitably pressing the pulse wave sensor 42 against the radial artery 54. In addition, the CPU 24 determines a relationship between blood pressure and pulse wave (hereinafter, referred to as the "BP-PW relationship"), based on the blood pressure values measured by using the cuff 10 and pulse wave signal SM* supplied from optimum pressure sensing element 60*. The CPU 24 periodically determines a systolic and a diastolic pressure value according to the BP-PW relationship based on magnitudes of the proper upper and lower peaks of each of the heartbeat synchronous pulses represented by pulse wave signal SM*, and commands a display 64 to successively indicate the blood pressure values determined (this process will be referred to as the "blood pressure monitoring").

In the meantime, according to the program stored in the ROM 26, the CPU 24 commands the RAM 28 to concurrently store pulse wave signals SM supplied from all the pressure sensing elements 60, in corresponding memory areas of the RAM 28 each of which is capable of storing pulse wave signal data corresponding to a predetermined number of heartbeats. While chamber pressure P is increased for determining optimum chamber pressure P*, or during the blood pressure monitoring, the CPU 24 checks if pulse wave signal SM* from optimum pressure sensing element 60* or selected one element 60a is abnormal or not. If the result of the checking is affirmative, the CPU 24 selects another pressure sensing element such that an amplitude of pulse wave signal SM from the selected another element is the greatest of the amplitudes of pulse wave signals SM which are stored in the RAM 28 concurrently with the abnormal pulse wave signal, and the CPU 24 changes optimum element 60* from the element 60a to the selected another element.

Figure 4A:
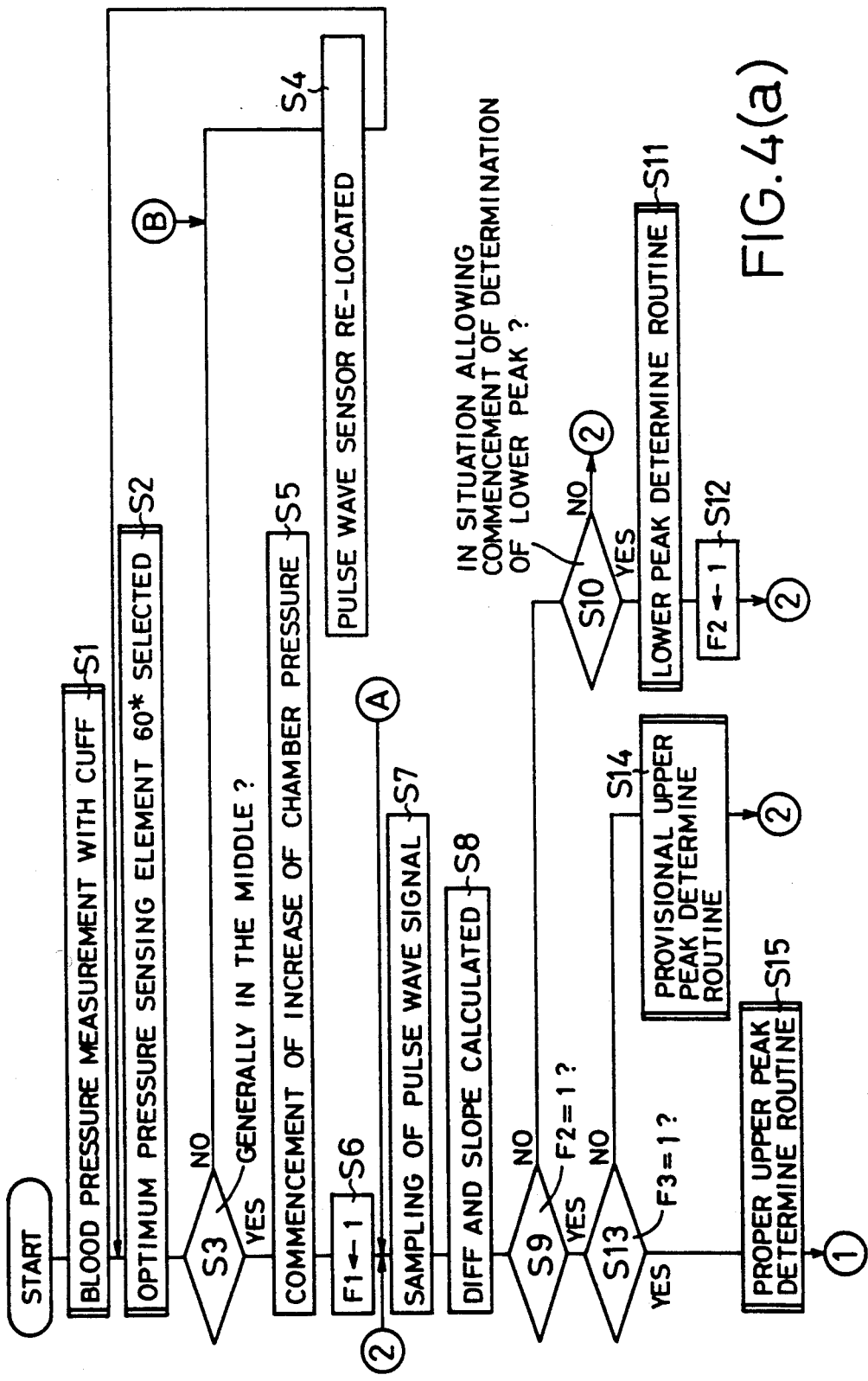
FIGS. 4(a) and 4(b) shows a flow chart according to which the monitoring system of FIG. 1 is operated.
Figure 4B:
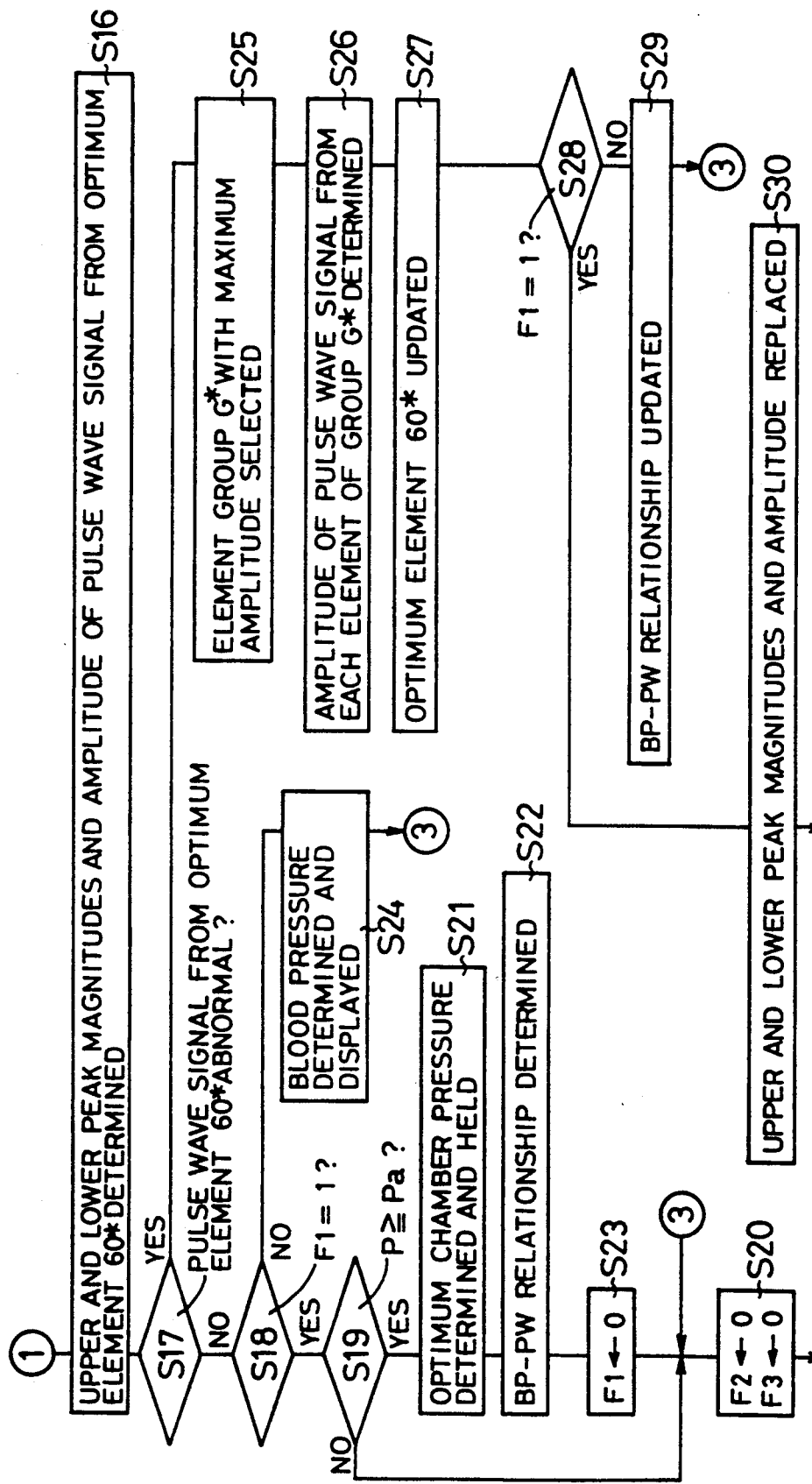

Referring next to FIGS. 4(a) and 4(b), there is shown a flow chart representing the program according to which is operated the blood pressure monitoring system constructed as described above.

First, the cuff 10 is wound around the upper arm 12 of a subject and the detector probe 33 is set on the wrist 32 of the subject. When electric power is applied to the present system through operation of a power switch (not shown), initialization is carried out on the system so that all the flags and counters that will be described hereinafter are reset to zero. The control of the CPU 24 begins with Step S1 in which a systolic and a diastolic blood pressure (mmHg) of the subject are determined by the previously-described oscillometric method in which the cuff 10 is used. Step S1 is followed by Step S2 in which chamber pressure P (i.e., pressure in the pressure chamber 44) is increased to a predetermined value, for determining an amplitude of pulse wave signal SM supplied from each of the pressure sensing elements 60 with chamber pressure P held at the predetermined value. In Step 2, one pressure sensing element 60a is selected as an optimum pressure sensing element 60* which provides pulse wave signal SM* whose amplitude is the greatest of all the amplitudes of pulse wave signals SM from the pressure sensing elements 60 of the element groups G1 ∝ G3.

Step S2 is followed by Step S3 in which it is judged whether or not optimum pressure sensing element 60*, namely, selected one element 60a is one located generally in the middle of the element arrays 60A. If the judgement in Step S3 is affirmative (YES), the control proceeds with Step S5. On the other hand, if the judgement is negative (NO), the control proceeds with Step S4 in which according to a predetermined algorithm the CPU 24 operates for discharging the fluid in the pressure chamber 44, and moving the pulse wave sensor 42 in a direction generally perpendicular to the radial artery 54 so that an element located generally in the middle of the element arrays 60A is selected as optimum element 60*. Subsequently the control goes back to Step S2.

Figure 8:
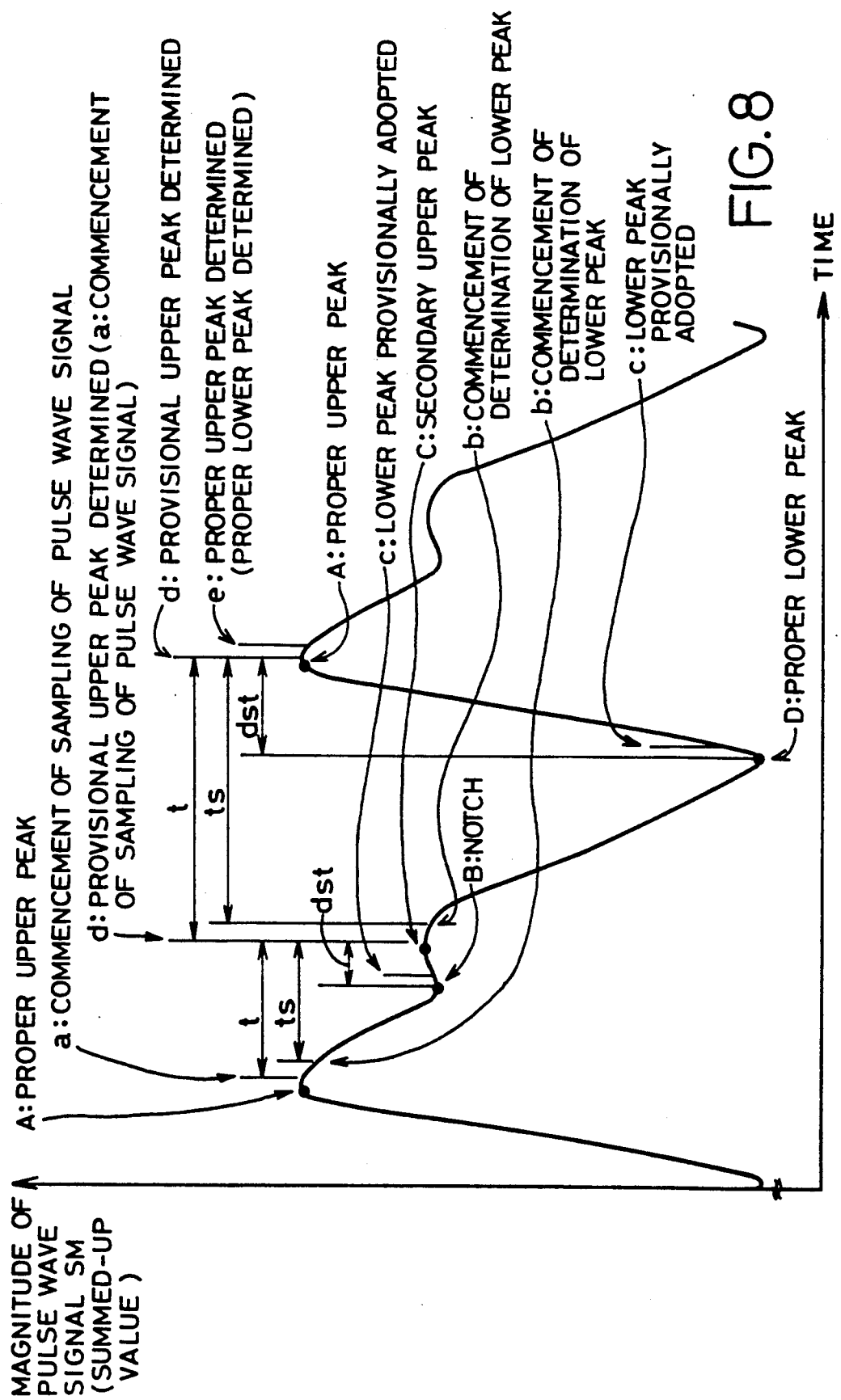
FIG. 8 shows an example of the arterial pulse wave obtained by summing up the signals supplied from the pressure sensing elements belonging to each of the element groups of the detector probe of FIG. 2.

In Step S5, the fluid in the pressure chamber 44 is discharged. Subsequently the pressure chamber 44 is supplied with the pressurized fluid from the electric pump 18 so that chamber pressure P is increased at a suitable rate. Step S5 is followed by Step S6 in which flag F1 is placed in the position, F=1, indicating that chamber pressure P is being increased. Step S6 is followed by Step S7 in which, while chamber pressure P is being increased, pulse wave signals SM supplied from all the pressure sensing elements 60 are concurrently stored in the corresponding memory areas in the RAM 28. In other words, the magnitude of pulse wave signal SM from each element 60 periodically is determined, and data of the determined magnitudes are timewise stored in the corresponding memory area of the RAM 28 (this process will be referred to as the "periodic data sampling"). The period is, for example, 5 ms (milliseconds). Step S7 is followed by Step S8 in which, with respect to each of the element groups G1–G3, the magnitudes sampled in Step S7 at a current cycle with respect to the pressure sensing elements 60 belonging to each element group G1-G3, are summed up. The summed-up value is stored in the RAM 28. The summed-up values collected over cycles provide a summed-up pulse wave as shown in FIG. 8. In Step S8, in addition, with respect to each element group G1-G3 a value, DIFF, is calculated by subtracting a summed-up value. obtained at the preceding cycle (i.e., 5 ms before) from the summed-up value obtained at the current cycle and a value, SLOPE, is calculated by subtracting, from the summed-up value obtained at the current cycle, a summed-up value obtained at a cycle prior by a predetermined number of periods or cycles (e.g., 8 cycles) to the current cycle ((i.e., 40 ms before).

Step S8 is followed by Step S9 in which it is judged whether or not flag F2 is in the position, F2=1, indicating that with respect to at least one of the element groups G1-G3 a lower peak has been determined on the summed-up pulse wave obtained in Step S7 with respect thereto. As described above, the summed-up pulse wave consists of the summed-up values obtained with respect to the pressure sensing elements 60 belonging to each element group G1-G3. If the judgement in Step S9 is negative, namely, if with respect to every element group G1-G3 no lower peak has been determined on the summed-up pulse wave thereof, the control goes to Step S10 in which it is judged whether or not at least one of the element groups G1-G3, or the summed-up pulse wave thereof, has come to a situation allowing commencement of a lower peak determination. Step S10 and other steps, SA1 (FIG. 5), SB1, SB5-SB10 (FIG. 6) and SC1, SC2 (FIG. 7), that will be described hereinafter are effected in such a manner that, if in each step an affirmative judgement is provided with respect to at least one of the element groups G1-G3, the control proceeds with the corresponding following step in which a judgement is made with respect to each of the at least one element group. In Step S10, an affirmative judgement is provided, for example, if negative SLOPEs have been obtained in Step S8 over eight or more successive cycles. If the judgement in Step S10 is negative, the control returns to Step S7 and the following steps. On the other hand, if the judgement in Step S10 is affirmative, the control goes to Step S11, that is, the lower peak determine routine. The present monitoring system is adapted such that, once the judgement in Step S10 is turned affirmative, affirmative judgements are provided over cycles until a lower peak is determined on the summed-up pulse wave of the at least one element group G1-G3.

Figure 5:
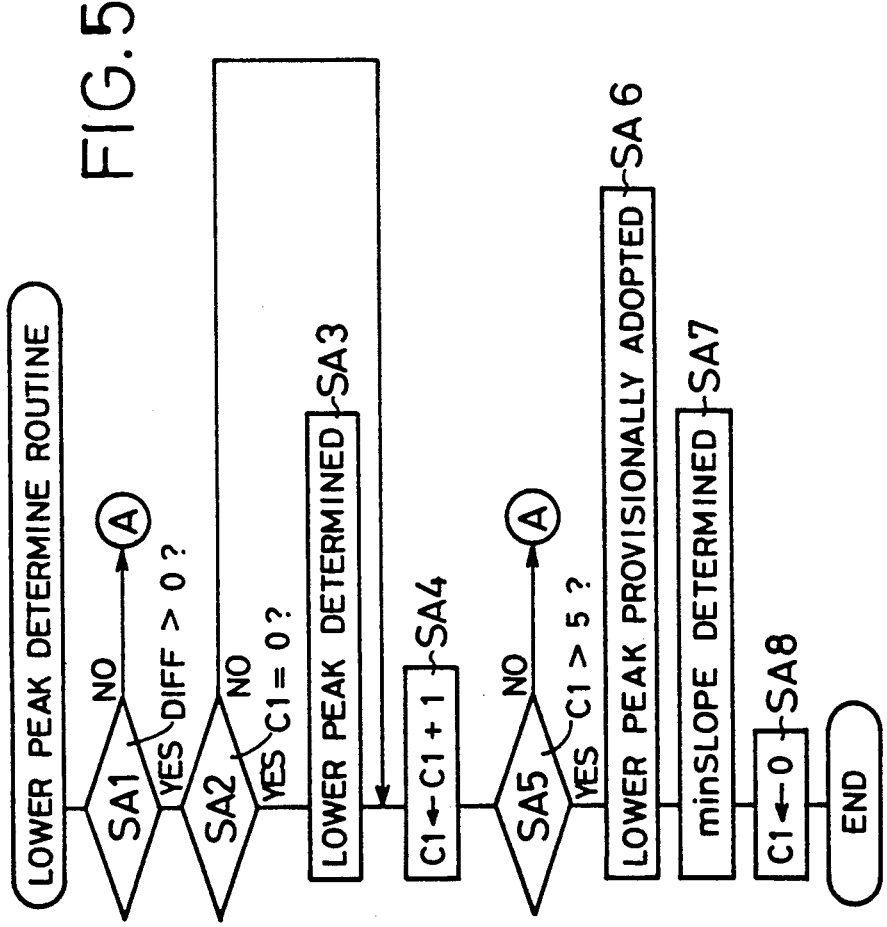
FIG. 5 shows a flow chart representing the lower peak determine routine of FIG. 4(a)

The lower peak determine routine of Step S10 is represented by a flow chart shown in FIG. 5. The control begins with Step SA1 in which it is judged whether or not a positive DIFF has been obtained in Step S8 at a current cycle. If the judgement in Step SA1 is negative, the control goes back to Step S7 and the following steps. On the other hand, if the judgement is affirmative, the control proceeds with Step SA2 in which it is judged whether or not counter C1 has counted none, namely, the content thereof is zero. Counter C1 counts the number of successive affirmative judgements provided in Step SA1 over successive cycles. If the judgement in Step SA2 is affirmative, namely, if the affirmative judgement provided in Step SA1 at the current cycle is the first one, the control goes to Step SA3 in which the summed-up value obtained in Step S8 at the preceding cycle is determined as a lower peak value. Step SA3 is followed by Step SA4 in which one is added to the content of counter C1, and subsequently in Step SA5 it is judged whether or not counter C1 has counted five, for example, namely, whether or not five or more successive affirmative judgements have been provided in Step SA1 over successive cycles.

If the judgement in Step SA5 is negative, the control goes back to Step S7 and the following steps. On the other hand, if the judgement is affirmative, the control goes to Step SA6 in which the lower peak determined in Step SA3 provisionally is adopted. Step SA6 is followed by Step SA7 in which is determined a value, minSLOPE, that is an absolute value of the smallest value of the negative SLOPEs obtained with respect to a portion of the summed-up pulse wave between the commencement of the present, lower peak determination (indicated at b in FIG. 8), and the provisionally adopted lower peak (indicated at B in FIG. 8). Step SA7 is followed by Step SA8 in which counter C1 is reset to zero. Once counter C1 begins to count, then the judgement in Step SA2 is found negative and the control skips Step SA3 and goes to Step SA4. The lower peak determine routine of Step S11 is followed by Step S12 in which flag F2 is placed in the position F2=1, and the control goes back to Step S7 and the following steps. In the present embodiment, Steps S9-S12 serve as means for determining a lower peak of a heartbeat synchronous pulse wave.

If flag F2 is in the position F2=1, the judgement in Step S9 is found affirmative, and the control proceeds with Step S13 in which it is judged whether or not flag F3 is in the position, F3=1, indicating that with respect to at least one of the element groups G1-G3 an upper peak has provisionally been determined on the summed-up pulse wave obtained with respect thereto. If the judgement in Step S13 is negative, namely, if with respect to every element group G1-G3 no provisional upper peak has been determined, the control goes to Step S14, that is, the provisional upper peak determine routine.

Figure 6:
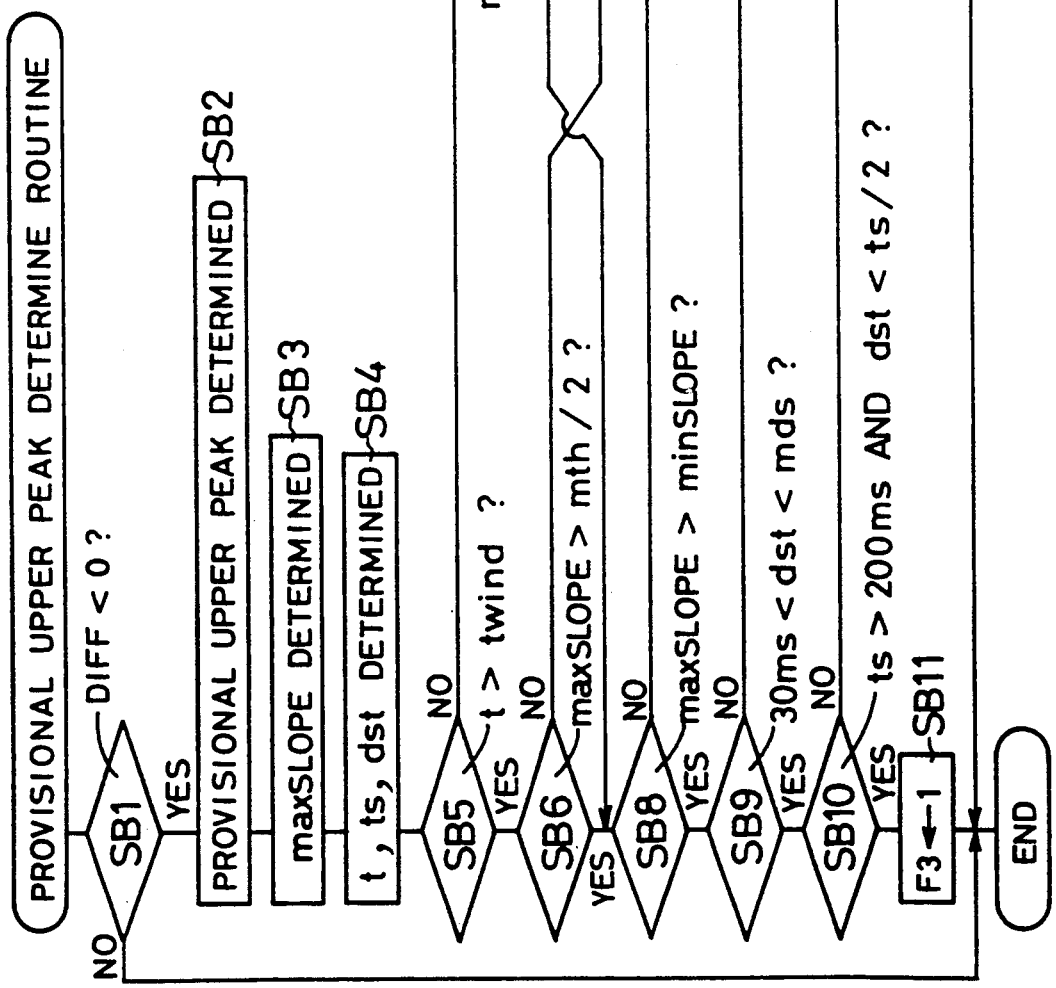
FIG. 6 shows a flow chart representing the upper peak determine routine of FIG. 4(a)

The provisional upper peak determine routine is represented by a flow chart shown in FIG. 6. Initially, in Step SB1 it is judged whether or not a negative DIFF has been obtained in Step S8 at a current cycle. If the judgement in Step SB1 is negative, the control goes back to Step S7 and the following steps. On the other hand, if the judgement is affirmative, the control goes to Step SB2 in which the summed-up value obtained in Step S8 at the preceding cycle provisionally is determined as an upper peak value, maxV. Steps SB1 and SB2 serve as means for determining a provisional upper peak of a heartbeat synchronous pulse wave.

Step SB2 is followed by Step SB3 in which is obtained a value, maxSLOPE, that is the greatest value of the positive SLOPEs obtained with respect to a portion of the summed-up pulse wave between the provisionally adopted lower peak and the provisional upper peak (indicated at d in FIG. 8). Step SB3 is followed by Step SB4 in which values, t, ts, dst, are determined on the summed-up pulse wave. Value t is defined as a period of time between the commencement of the periodic data sampling (indicated at a in FIG. 8), and the sampling time of the provisional upper peak. Value ts is defined as a period of time between the commencement of the lower peak determination and the sampling time of the provisional upper peak. Value dst is defined as a period of time between the sampling time of the provisionally adopted lower peak and the sampling time of the provisional upper peak. Values t, ts, dst are indicated in FIG. 8.

Step SB4 is followed by Step SB5 in which it is judged whether or not value t obtained in Step SB4 at the current cycle is greater than a parameter, twind. Parameter twind is defined by the following expression: twind = 4/5 × $ts_{-1}$, where $ts_{-1}$ is a value ts which has been determined with respect to the preceding, proper upper peak determined in Step S15 that will be described hereinafter. The initial value, zero, is predetermined for parameter twind. If the judgement in Step SB5 is affirmative the control goes to Step SB6, while if the judgement is negative the control goes to Step SB7. In Step SB6 it is judged whether or not value maxSLOPE determined in Step SB2 at the current cycle is greater than a value, $\frac{1}{2}$×mth, while in Step SB7 it is judged whether or not the value maxSLOPE is greater than a value, mth. Parameter mth is defined by the following expression: mth = 7/10 × $maxSLOPE_{-1}$, where $maxSLOPE_{-1}$ is a value maxSLOPE which has been determined with respect to the preceding proper upper peak. The initial value, zero, is predetermined for parameter mth. If the judgement in Step SB6 or Step SB7 is affirmative, the control goes to Step SB8 in which it is judged whether or not value maxSLOPE determined in Step SB3 at the current cycle is greater than a value minSLOPE determined in Step SA7 with respect to the provisionally adopted lower peak preceding the present, provisional upper peak. If the judgement in Step SB8 is affirmative, the control goes to Step SB9 in which it is judged whether or not value dst obtained in Step SB4 at the current cycle is greater than a predetermined time, for example, 30 ms and smaller than a parameter, mds. Parameter mds is defined by the following expression: mds = $\frac{1}{2}$ × $ts_{-1}$, and falls within the range of 500 to 200 ms. The initial value, 500 ms, is predetermined for parameter mds. If the judgement in Step SB9 is affirmative, the control goes to Step SB10 in which it is judged whether or not value ts obtained in Step SB4 at the current cycle is greater than a predetermined value, for example, 200 ms and simultaneously value dst obtained in Step SB4 at the current cycle is smaller than a half of the value ts. If affirmative judgements are provided in Step SB6 or SB7 and Steps SB8, SB9, SB10, the control goes to Step SB11 in which flag F3 is placed in the position F3 = 1 indicating that a provisional upper peak has been determined on the summed-up pulse wave obtained with respect to at least one of the element groups G1-G3. Subsequently the control goes back to Step S7 and the following steps. If flag F3 is in the position F3 = 1, the judgement in Step S13 is found affirmative, and the control goes to Step S15, that is, the proper upper peak determine routine.

If a negative judgement is provided in any of Steps SB6-SB10, it means that the provisional upper peak determined in Step SB2 at the current cycle is a secondary upper peak indicated at C in FIG. 8, not a proper upper peak indicated at A, and that the provisionally adopted lower peak preceding the provisional upper peak is a notch indicated at B, not a proper lower peak indicated at D. In this case, the control goes to Step SB12 in which flag F2 is placed in the position, F2 = 0, indicating a lower peak has not been determined yet. Subsequently the control goes back to Step S7 and the following steps so as to determine another lower peak. Steps SB5-SB10 serve as means for preventing a secondary upper peak from erroneously being determined as a proper upper peak and, in addition, a notch from erroneously being determined as a proper lower peak. Steps SB6-SB8 utilize value maxSLOPE that is the greatest value of the values SLOPE obtained with respect to a portion of the summed-up pulse wave between the provisionally adopted lower peak and the provisional upper peak.

Figure 7:
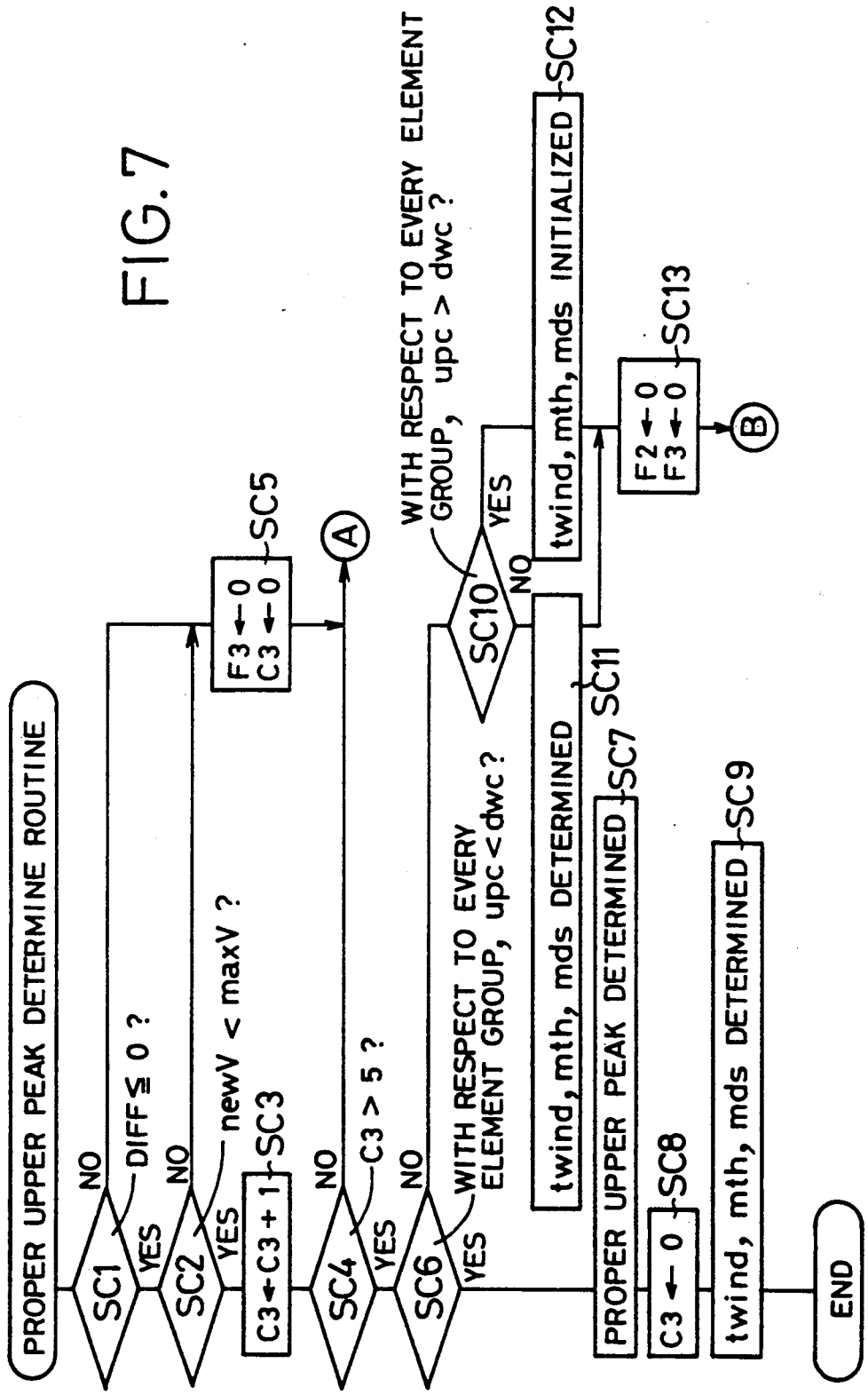
FIG. 7 shows a flow chart representing the proper upper peak determine routine of FIG. 4(a)

The proper upper peak determine routine is represented by a flow chart shown in FIG. 7. Initially, the control begins with Step SC1 in which it is judged whether or not a negative or zero DIFF has been obtained in Step S8 at a current cycle. If the judgement in Step SC1 is affirmative, the control goes to Step SC2 in which a summed-up value, newV, obtained in Step S8 at a current cycle is smaller than value maxV of the provisional upper peak determined in Step S14. If the judgement in Step SC2 is affirmative, the control goes to Step S3 in which counter C3 counts one. Counter C3 counts the number of successive cycles at which affirmative judgements are provided in both Steps SC1 and SC2. Step SC3 is followed by Step SC4 in which it is judged whether or not counter C3 has counted five. If the judgement in Step SC4 is negative, the control goes back to Step S7 and the following steps. If the judgement in either of Steps SC1 and SC2 is negative, the control goes to Step SC5 in which flag F3 is placed in the position, F3 = 0, indicating that a provisional upper peak has not been determined yet, and counter C3 is reset to zero. Subsequently the control goes back to Step S7 and the following steps so as to determine another provisional upper peak.

If the judgement in Step SC4 is affirmative, the control goes to Step SC6 in which it is judged whether or not, with respect to every element group G1-G3 a value, upc, is smaller than a value, dwc. Value upc is defined as the number of positive or zero SLOPEs out of the SLOPEs obtained between the commencement of the lower peak determination, and a current cycle (indicated at e in FIG. 8), while value dwc is defined as the number of the remaining, negative SLOPEs out of the same SLOPEs. If the judgement in Step SC6 is affirmative, it means that with respect to every element group G1-G3 the phase of the summed-up pulse wave obtained with respect thereto is normal, or not reversed, as shown in FIG. 8. In this case, the control goes to Step SC7 in which the provisional upper peak is determined as a proper upper peak of a pulse of the arterial pulse wave. In addition, the affirmative judgement in Step SC6 means that the provisionally adopted lower peak preceding the provisional upper peak is a proper lower peak of the arterial pulse wave. Step SC7 is followed by Step SC8 in which counter C3 is reset to zero, and subsequently in Step SC9 values twind, mth, mds are determined with respect to the present proper upper peak. These values are utilized for determining proper upper and lower peaks of a subsequent pulse of the arterial pulse wave. Step SC9 is followed by Step S16 of FIG. 4(b).

On the other hand, if the judgement in Step SC6 is negative, the control goes to Step SC10 in which it is judged whether or not with respect to every element group G1-G3 the number upc is greater than the number dwc. If the judgement in Step SC10 is negative, it means that with respect to at least one of the element groups G1-G3 the phase of the summed-up pulse wave thereof is normal. In this case, the control goes to Step SC11 in which values twind, mth, mds are determined based on the normal summed-up pulse wave. If the judgement in Step SC10 is affirmative, it means that with respect to every element group G1-G3 the phase of the summed-up pulse wave is reversed. The phase-reversed pulse wave would be generally symmetrical with the non-reversed pulse wave, with respect to a line parallel to the axis of time of FIG. 8. The phase-reversed pulse wave is not suitable to use for determining proper upper and lower peaks of the arterial pulse wave. In this case, therefore, the control goes to Step SC12 in which parameters twind, mth, mds are initialized to the initial values zero, zero, 500 ms, respectively. A comparatively large displacement of the pulse wave sensor 42 relative to the radial artery 54 as viewed in a direction generally perpendicular to the artery 54 due to, for example, physical motion of the subject, may cause the pressure sensing elements 60 to be moved to a location directly above a radius or tendon (not shown), possibly resulting in producing a phase-reversed pulse wave. Step SC12 is followed by Step SC13 in which flags F2 and F3 are placed in the positions F2=0 and F3=0, respectively, and subsequently the control returns to Step S4 to re-locate the pulse wave sensor 42 so that a pressure sensing element generally located in the middle of the element arrays 60A is selected as optimum element 60*. Steps S14 (except for Steps SB1 and SB2) and S15 serve as means for judging whether or not a provisional upper peak determined in Steps SB1 and SB2 is a proper upper peak of a pulse of a heartbeat synchronous pulse wave.

The proper upper peak determine routine of Step S15 is followed by Step S16 in which an upper and a lower peak of pulse wave signal SM* from optimum pressure sensing element 60* are determined based on the sampling times of the proper lower and upper peaks determined in Step S15, and an amplitude of pulse wave signal SM* is determined from magnitudes of the upper and lower peaks. The upper and lower peak magnitudes and the amplitude are stored in the RAM 28. In the case where chamber pressure P is being increased for determining optimum chamber pressure P*, chamber pressure values (P) represented by pressure signal SP at the sampling times of the upper and lower peak are also stored in the RAM 28.

Step S16 is followed by Step S17 in which it is judged whether or not pulse wave signal SM* from optimum pressure sensing element 60* or selected one element 60a is abnormal. An affirmative judgement is provided, for example, if the amplitude determined in Step S16 is smaller than a value which is predetermined based on an amplitude estimated at optimum chamber pressure P* on the subject. If the judgement in Step S17 is negative, the control goes to Step S18 in which it is judged whether or not flag F1 is in the position F1=1, namely, whether or not chamber pressure P is being increased. If the judgement in Step S18 is affirmative, the control goes to Step S19 in which it is judged whether or not chamber pressure P has exceeded a predetermined value Pa. If the judgement in Step S19 is negative, the control goes to Step S20 in which flags F2 and F3 are placed in the positions F2=0 and F3=0, respectively, and subsequently the control goes to Step S7 and the following steps. If the judgement in Step S19 is affirmative, namely, if chamber pressure P has exceeded value Pa, the control goes to Step S21 in which an optimum chamber pressure P* corresponding to an optimum pressing force for most suitably pressing the pulse wave sensor 42 against the radial artery 54, is determined based on, for example, variations in magnitude of lower peak and amplitude of pulse wave signal SM* from optimum element 60* which variations are detected while chamber pressure P is being increased. In addition, in Step S21 chamber pressure P is maintained at optimum pressure value P* determined.

Step S21 is followed by Step S22 in which a BP-PW relationship is determined based on the systolic and diastolic pressure values determined in Step S1 by using the cuff 10, and magnitudes of the upper and lower peaks of pulse wave signal SM* from optimum pressure sensing element 60* which peaks are sampled when chamber pressure P is equal to optimum pressure value P*. Step S22 is followed by Steps S23 and S20 in which flags F1, F2, F3 are placed in the positions F1=0, F2=0, F3=0, respectively. Subsequently, the control goes back to Step S7 and the following steps. Since a negative judgement is provided in Step S18, the control goes to Step S24 in which a systolic and a diastolic pressure value are determined according to the BP-PW relationship determined in Step S22 based on the upper and lower peaks magnitudes determined in Step S16 at a current cycle on pulse wave signal SM* from optimum pressure sensing element 60*, and the display 64 indicates the blood pressure values determined. Step S24 is followed by Step S20, and subsequently the control goes back to Step S7 and the following steps. By repeating Steps S7-S18, Step S24 and S20, systolic and diastolic pressure values periodically are determined and displayed. In this way, blood pressure monitoring of the subject is carried out.

On the other hand, if the judgement in Step S17 is affirmative, namely, if, while chamber pressure P is increased for determining optimum chamber pressure P*, or during the blood pressure monitoring, it is judged that pulse wave signal SM* from optimum pressure sensing element 60* or selected one element 60a is abnormal, the control goes to Step S25 in which with respect to each of the elements groups G1-G3 a value is obtained by summing up the amplitudes of pulse wave signals SM from the pressure sensing elements 60 belonging to each element group G1-G3 which signals are stored in the RAM 28 concurrently with the abnormal pulse wave signal, and one element group is selected from the element groups G1-G3 such that the summed-up value obtained with respect to the selected one element group is the greatest of all the summed-up values obtained with respect to the element groups G1-G3. Step S25 is followed by Step S26 in which upper and lower peaks of pulse wave signal SM from each of the pressure sensing elements 60 belonging to the selected one element group G1-G3, are determined based on the sampling times of the proper upper and lower peaks determined in Step S15, and an amplitude of pulse wave signal SM from each element 60 is determined from magnitudes of the upper and lower peak. Step S26 is followed by Step S27 in which another pressure sensing element is selected as optimum pressure sensing element 60* in place of the selected one element 60a such that the amplitude of the selected another element is the greatest of all the amplitudes determined in Step S26. Step S27 is followed by Step S28 in which it is judged whether or not flag F1 is in the position F1=1, namely, whether or not chamber pressure P is being increased. If the judgement in Step S28 is negative, namely, in the case where chamber pressure P is not being increased and therefore blood pressure monitoring is being carried out with chamber pressure P held at optimum pressure value P*, the control goes to Step S29 in which the BP-PW relationship determined in Step S22 is updated based on the systolic and diastolic blood pressure values determined in Step S1 by using the cuff 10, and the upper and lower peaks magnitudes determined on pulse wave signal SM* from optimum pressure sensing element 60* updated in Step S27. Step S29 is followed by Step S20, and subsequently the control goes back to Step S7 and the following steps. On the other hand, if the judgement in Step S28 is affirmative, namely, in the case where chamber pressure P is being increased for determining optimum chamber pressure P*, the control goes to Step S30 in which the upper and lower peaks magnitudes and the amplitude determined and stored in Step S16 are replaced by the upper and lower peaks magnitudes and the amplitude determined on pulse wave signal SM* from optimum element 60* updated in Step S27. Step S30 is followed by Step S20, and subsequently the control returns to Step S7 and the following steps.

As is apparent from the foregoing description, Steps SB5-SB10 in the provisional upper peak determine routine (Step S14) serve for preventing a lower peak provisionally adopted in the lower peak determine routine (Step S11) and a provisional upper peak determined in Step SB2 from erroneously being identified as proper lower and upper peaks of arterial pulse wave to be detected. In other words, Steps SB5-SB10 serve for identifying a lower peak provisionally adopted in Step S11 and a provisional upper peak determined in Step SB2, as a notch and a secondary upper peak of the arterial pulse wave. In the present embodiment, if the provisionally adopted lower peak and the provisional upper peak are not identified as proper lower and upper peaks, those peaks are discarded and further operation is effected to determine other lower and upper peaks. In almost cases, Steps SB6-SB8 serve for excluding notches and secondary upper peaks. In the meantime, in the event that the magnitude of a secondary upper peak is greater than that of a proper upper peak due to, for example, Valsalva's test, Steps SB9 and SB10 serve for excluding the secondary upper peak (and the notch preceding the peak) because in this event, normally, time dst becomes much longer. Thus, proper upper and lower peaks are determined with sufficient reliability on the summed-up pulse wave provided by the values obtained by summing up the magnitudes of pulse wave signals SM belonging to each of the element groups G1-G3. Based on the sampling times of the proper upper and lower peaks, upper and lower peaks are determined with sufficient accuracy on pulse wave signal SM* from optimum pressure sensing element 60*. Therefore, with high accuracy, optimum chamber pressure P* is determined and blood pressure monitoring is carried out.

If, during the blood pressure monitoring, pulse wave signal SM* from optimum pressure sensing element 60* is judged as being abnormal, another pressure sensing element is selected as a new optimum pressure sensing element 60* such that the amplitude of the selected another element is the greatest of the amplitudes of pulse wave signals SM which are stored in the RAM 28 concurrently with the abnormal pulse wave signal. In this way, the optimum pressure sensing element is updated in a reduced time as compared with the time needed for updating optimum element 60* by determining the amplitudes of pulse wave signals supplied from the pressure sensing elements after the judgement of pulse wave signal from the abnormal optimum element. Consequently, the blood pressure monitoring is resumed instantly.

In the case where chamber pressure 44 is being increased for determining optimum chamber pressure P*, if pulse wave signal SM* from optimum pressure sensing element 60* is judged as being abnormal, another pressure sensing element is selected instantly as a new optimum pressure sensing element 60* in a manner similar to that for the blood pressure monitoring, namely, by utilizing pulse wave signals SM which have been stored in the RAM 28 concurrently with the abnormal pulse wave signal. Further, the upper and lower peaks magnitudes and the amplitude determined with respect to pulse wave signal SM* from the new optimum element 60* which signal has been stored in the RAM 28 concurrently with the abnormal pulse wave signal, are used in place of those determined with respect to the abnormal pulse wave signal. Consequently, chamber pressure P can continuously be increased for determining optimum chamber pressure P*, without having to cease even when pulse wave signal SM* from optimum pressure sensing element 60* is judged as being abnormal, so that the pulses of arterial pulse wave needed for determining optimum chamber pressure P* continuously are obtained without losing any pulses at the time of updating of optimum element 60*. The time needed for determining optimum chamber pressure P* is not increased by the updating of optimum element 60*.

In the present embodiment, if pulse wave signal SM* from optimum pressure sensing element 60* is judged as being abnormal, a value is determined by summing up the amplitudes of pulse wave signals SM from pressure sensing elements 60 belonging to each of the element group G1-G3, and one group is selected from the three groups G1-G3 such that the summed-up value obtained from the selected one group is the greatest of all the summed-up values of the three groups G1-G3. Further, the amplitude of pulse wave signal SM from each of the elements 60 belonging to the selected one group G1-G3 is determined, and another pressure sensing element is selected as a new optimum pressure sensing element such that the amplitude of the selected another element is the greatest of all the amplitudes determined. Thus, optimum element 60* is updated in a decreased time as compared with the time needed for updating optimum element 60* by determining the amplitudes of pulse wave signals SM from the pressure sensing elements 60 of the element groups G1-G3.

Furthermore, if in the proper upper peak determine routine (Step S15) it is judged that the phase of the summed-up pulse wave obtained from at least one of the element groups G1-G3 is reversed, the pulse wave sensor 42 is driven to be re-located relative to the radial artery 54. Since Step S17 is effected, after Step S15, to judge the abnormality of pulse wave signal SM* from optimum pressure sensing element 60*, optimum element 60* is one generally located in the middle of the element arrays 60A. Therefore, if the abnormality of pulse wave signal from optimum element 60* is found in Step S17 and another element is selected as a new optimum element 60* in Step 27, the selected another element would probably be one generally located in the middle of the element arrays 60A. The new optimum element 60* would produce an excellent pulse wave signal if it is located generally in the middle of the element arrays 60A.

In the present embodiment, pulse wave signals SM from all the pressure sensing elements 60 are concurrently stored in the RAM 28 and proper upper and lower peaks are determined on the summed-up pulse waves obtained from the element groups G1-G3. Based on the sampling times of the proper upper and lower peaks, upper and lower peaks are determined on pulse wave signal SM* from optimum pressure sensing element 60*, for blood pressure monitoring, and upper and lower peaks are determined on pulse wave signals SM from the pressure sensing elements 60 of each of the element groups G1-G3, for updating optimum element 60*. Thus, even in the event that the amplitude of the abnormal pulse wave signal is substantially zero and therefore proper upper and lower peaks cannot be determined on the signal, a new optimum element 60* can be selected. On the other hand, in the case where with respect to only optimum pressure sensing element 60* Steps S8-S15 are effected for determining proper upper and lower peaks on pulse wave signal SM* supplied therefrom, it is impossible to select a new optimum element 60* if the amplitude of the abnormal pulse wave signal is almost zero, because proper upper and lower peaks and the sampling times thereof cannot be determined on the signal. As described above, the sampling times of the proper upper and lower peaks must be determined for finding upper and lower peaks of pulse wave signals SM which have been stored in the RAM 28 concurrently with the abnormal pulse wave signal, for selecting a new optimum element 60*.

In addition, in the present embodiment, upper and lower peaks of arterial pulse wave are determined based on changes of sign of value DIFF that is obtained by subtracting, from the magnitude of pulse wave signal (i.e., summed-up value of the magnitudes of pulse wave signals SM from the pressure sensing elements 60 belonging to each of the element groups G1-G3) determined at a current cycle, the magnitude of pulse wave signal determined at the preceding cycle. Therefore, the determination of upper and lower peaks are free from influences of possibly mixed low frequency noise.

While the present invention has been described in its presently preferred embodiment, the invention may otherwise be embodied.

For example, while in the illustrated embodiment value maxSLOPE is used in Steps SB6-SB8 of the provisional upper peak determine routine, for preventing a provisional upper peak determined in Step SB2 from erroneously being identified as a proper upper peak, it is possible to use, in place of value maxSLOPE, an average of the values SLOPE obtained with respect to a portion of the summed-up pulse wave (or summed-up values) between a provisionally adopted lower and a following provisional upper peak.

In addition, in the case where the period of sampling of pulse wave signals SM is considerably longer than the period used in the illustrated embodiment (i.e., 5 ms), it is possible to utilize, in place of value SLOPE, value DIFF in Steps SB8-SB10 for preventing a provisional upper peak determined in Step SB2 from erroneously being identified as a proper upper peak.

Furthermore, in the illustrated embodiment, it is possible to omit Steps SB9 and SB10 from the provisional upper peak determine routine. In other words, either Steps SB5-SB7 or Step SB8 serve(s) for preventing a provisional upper peak from erroneously being determined as a proper upper peak.

Although in the illustrated embodiment a plurality of pressure sensing elements 60 are grouped into three element groups G1, G2, G3 and proper upper and lower peaks are determined on the summed-up pulse waves obtained with respect to the element groups G1-G3, it is possible to group the elements 60 into a different number of groups, or not to group the elements 60. In the last case, proper upper and lower peaks are determined on pulse wave signal SM from each of the elements 60. Alternatively, it is possible to use a single pressure sensing element so that proper upper and lower peaks are determined on pulse wave signal SM from the single element.

The illustrated blood pressure monitoring system may further include means for sounding an alarm or means for displaying a warning if the abnormality of pulse wave signal SM* from optimum pressure sensing element 60* is identified in Step S17. Since the abnormality of pulse wave signal SM* can be caused by a disorder of optimum element 60* itself, it is necessary to check the element generating the abnormal pulse wave signal.

In the illustrated embodiment, the pulse wave sensor 42 is driven to be re-located relative to the radial artery 54 if the phase of the summed-up pulse wave determined with respect to at least one of the element groups G1-G3 is reversed, and optimum pressure sensing element 60* is updated if with respect to every element group G1-G3 the phase of the summed-up pulse wave is not reversed and the abnormality of pulse wave signal SM* from optimum element 60* is identified. However, it is possible that the illustrated monitoring system be adapted to update optimum pressure sensing element 60* if pulse wave signal SM from optimum element 60* is judged as being abnormal, and re-locate the pulse wave sensor 42 if an updated optimum element 60* is one which is not located generally in the middle of the element arrays 60A.

While in the illustrated embodiment the present embodiment is applied to the arterial pulse wave detecting apparatus incorporated in the blood pressure monitoring system, it is possible to apply the principle of the present invention to other types of heartbeat synchronous pulse wave detecting apparatus such as an electrocardiograph and a photoelectric pulse wave detector. It goes without saying that the invention can be applied to an apparatus for monitoring a heartbeat synchronous pulse wave itself, in particular for making a diagnosis on the heart of a subject.

While the illustrated monitoring system uses the pressure sensing elements 60 formed of semiconductors such as pressure sensing diodes, it is possible to use other types of pressure sensing elements.

Furthermore, the illustrated monitoring system can be adapted to detect a heartbeat synchronous pulse wave from a carotid artery or a dorsal pedal artery other than the radial artery 54.

It is to be understood that the present invention may be embodied with other changes, improvements and modifications that may occur to those skilled in the art without departing from the spirit and scope of the invention as defined in the pending claims.

What is claimed is:

1. An apparatus for detecting a pulse wave produced from a subject in synchronous relationship with heartbeats of the subject, the heartbeat synchronous pulse wave consisting of a plurality of successive pulses each of which corresponds to a heartbeat and has at least one upper peak including a proper upper peak and at least one lower peak including a proper lower peak, the apparatus comprising:

probe means for sensing a heartbeat synchronous pulse wave transmitted thereto and generating a signal representative of the sensed pulse wave;

sampling means for periodically determining a magnitude of said signal;

determining means for determining a lower peak and a following upper peak of said heartbeat synchronous pulse wave, based on variation of the magnitudes determined by said sampling means;

calculating means for calculating a plurality of values, SLOPE, by subtracting, from each of the magnitudes determined by said sampling means, a magnitude of said signal determined by said sampling means prior by a predetermined number of periods to said each of the magnitudes; and judging means for judging whether or not said following upper peak is a proper upper peak of a pulse of said heartbeat synchronous pulse wave, based on the plurality of values calculated by said calculating means with respect to a portion of said signal between said lower peak and said following upper peak.

2. The apparatus as set forth in claim 1, wherein said judging means further judges whether or not said lower peak is a proper lower peak of said heartbeat synchronous pulse wave, said judging means judging said lower peak as said proper lower peak if said judging means judges said following upper peak as said proper upper peak.

3. The apparatus as set forth in claim 1, wherein said judging means comprises means for determining a value, maxSLOPE, which is the greatest value of the plurality of values, SLOPE, obtained by said calculating means with respect to said portion of said signal between said lower peak and said following upper peak.

4. The apparatus as set forth in claim 3, wherein said judging means further comprises:

means for determining a time period, t, between commencement of the periodic magnitude sampling of said sampling means and the time of sampling of said following upper peak;

means for determining a time period, ts, between commencement of the lower peak determination of said determining means and the time of sampling of said following upper peak, said lower peak determination being commenced if negative SLOPEs are obtained by said calculating means over a predetermined number of successive cycles of said periodic magnitude sampling; and means for judging whether or not said value t is greater than a value, twind, said value twind being defined by the following expression: twind = $4/5 \times ts_{-1}$, where $ts_{-1}$ is a value ts which is determined with respect to a proper upper peak preceding said following upper peak.

5. The apparatus as set forth in claim 4, wherein said judging means further comprises means for, if said value t is judged not to be greater than said value twind, judging whether or not said value maxSLOPE is greater than a value, mth, said value mth being defined by the following expression: mth = $7/10 \times$ maxSLOPE$_{-1}$, where maxSLOPE$_{-1}$ is a value maxSLOPE which is determined with respect to a proper upper peak preceding said following upper peak, said judging means judging that said following upper peak is not said proper upper peak, if said value maxSLOPE is judged not to be greater than said value mth.

6. The apparatus as set forth in claim 4, wherein said judging means further comprises means for, if said value t is judged to be greater than said value twind, judging whether or not said value maxSLOPE is greater than a value, mth/2, said value mth being defined by the following expression: mth = $7/10 \times$ maxSLOPE$_1$, where maxSLOPE$_1$ is a value maxSLOPE which is determined with respect to said proper upper peak preceding said following upper peak, said judging means judging that said following upper peak is not said proper upper peak, if said value maxSLOPE is judged not to be greater than said value mth/2.

7. The apparatus as set forth in claim 3, wherein said judging means further comprises:

means for determining a value, minSLOPE, which is an absolute value of the smallest value of the values SLOPE obtained by said calculating means with respect to a portion of said signal between commencement of the lower peak determination of said determining means, and said lower peak, said lower peak determination being commenced if negative SLOPEs are obtained by said calculating means over a predetermined number of successive cycles of said periodic magnitude sampling; and means for judging whether or not said value maxSLOPE is greater than said value minSLOPE, said judging means judging that said following upper peak is not said proper upper peak, if said value maxSLOPE is judged not to be greater than said value minSLOPE.

8. The apparatus as set forth in claim 3, wherein said judging means further comprises:

means for determining a time period, dst, between the time of sampling of said lower peak and the time of sampling of said following upper peak; and means for judging whether or not said value dst is greater than a predetermined time and smaller than a value, mds, said value mds being defined by the following expression: mds = $\frac{1}{2} \times ts_{-1}$, where $ts_{-1}$ is a value ts which is determined with respect to a proper upper peak preceding said following upper peak, said value mds falling within a range of 500 to 200 ms, said judging means judging that said following upper peak is not said proper upper peak, if said value dst is judged either not to be greater than said predetermined value or not to be smaller than said value mds.

9. The apparatus as set forth in claim 3, wherein said judging means further comprises:

means for determining a time period, ts, between commencement of the lower peak determination of said determining means and the time of sampling of said following upper peak, said lower peak determination being commenced if negative SLOPEs are obtained by said calculating means over a predetermined number of successive cycles of said periodic magnitude sampling;

means for determining a time period, dst, between the time of sampling of said lower peak and the time of sampling of said following upper peak; and means for judging whether or not said value ts is greater than a predetermined value and said value dst is smaller than a value, ts/2, said judging means judging that said following upper peak is not said proper upper peak, either if said value value ts is judged not to be greater than said predetermined value, or if said value dst is judged not to be smaller than said value ts/2.

10. The apparatus as set forth in claim 1, wherein said determining means comprises:

means for calculating a value, DIFF, by subtracting, from said each of the magnitudes determined by said sampling means, a magnitude of said signal determined by said sampling means prior by one period to said each of the magnitudes;

means for determining, as said lower peak, a magnitude of said signal determined by said sampling means by which magnitude the sign of said value DIFF is changed from negative to positive; and means for determining, as said following upper peak, a magnitude of said signal determined by said sampling means by which magnitude the positive sign of said value DIFF is changed to negative.

11. The apparatus as set forth in claim 1, further comprising means for judging whether or not said probe means is located at an appropriate position on a body surface of said subject, said means judging that said probe means is located at said appropriate portion, if a value, upc, is smaller than a value, dwc, said value upc being defined as a number of positive or zero SLOPEs out of the plurality of values SLOPE obtained between commencement of the lower peak determination of said determining means, and said following upper peak, said lower peak determination being commenced if a negative SLOPE is obtained by said calculating means over a predetermined number of successive cycles of said periodic magnitude sampling, said value dwc being defined as a number of the remaining, negative SLOPEs out of said values SLOPE; and displacing means for, if said probe means is judged not to be located at said appropriate position, displacing said probe means to said appropriate position.

12. The apparatus as set forth in claim 1, wherein said probe means comprises a single pressure sensing element, said sampling means periodically determining a magnitude of the signal generated by said pressure sensing element.

13. The apparatus as set forth in claim 1, wherein said probe means comprises a plurality of pressure sensing elements which are grouped into a plurality of element groups, said sampling means periodically determining a magnitude of the signal generated by each of said pressure sensing elements belonging to each of said element groups, and calculating, with respect to each of said element groups, a value by summing up the magnitudes determined by said sampling means, said calculating means calculating said plurality of values SLOPE by subtracting, from each of the summed-up value obtained by said sampling means, a summed-up value obtained by said sampling means prior to said predetermined number of periods to said each of the summed-up values, said judging means providing an affirmative judgement if, with respect to at least one of said element groups, said following upper peak is judged as said proper upper peak based on the plurality of values SLOPE obtained by said calculating means between said lower peak and said following upper peak.

* * * * *